United States Patent [19]
Li

[11] Patent Number: 6,129,762
[45] Date of Patent: *Oct. 10, 2000

[54] ANCHOR AND METHOD FOR SECUREMENT INTO A BORE

[75] Inventor: Lehmann K. Li, Milford, Conn.

[73] Assignee: Li Medical Technologies, Inc., Shelton, Conn.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/741,000

[22] Filed: Nov. 5, 1996

Related U.S. Application Data

[63] Continuation of application No. 08/294,067, Aug. 22, 1994, Pat. No. 5,645,589.

[51] Int. Cl.[7] .......................................... A61F 2/08
[52] U.S. Cl. ........................... 623/13.11; 606/63; 606/72; 411/55
[58] Field of Search .............................. 623/13.11, 16.11; 606/95, 72, 73, 60, 62, 63; 411/24, 25, 26, 55, 80

[56] References Cited

U.S. PATENT DOCUMENTS

| | | | |
|---|---|---|---|
| 4,738,255 | 4/1988 | Goble et al. | 623/16 |
| 4,772,286 | 9/1988 | Goble et al. | 623/13 |
| 5,643,266 | 7/1997 | Li | 623/13 |
| 5,645,589 | 7/1997 | Li | 623/16 |

*Primary Examiner*—Bruce Snow
*Attorney, Agent, or Firm*—Ostrolenk, Faber, Gerb & Soffen, LLP

[57] ABSTRACT

An anchor and method for securement into a bore in a medium. The anchor has a first generally hollow cylindrical section having a first plurality of spaced longitudinally directed fingers and a second generally hollow cylindrical section having a second plurality of spaced longitudinally directed fingers. The first and second sections are arranged opposed to each other with the fingers of each section being interdigitated with the fingers of the other section. The first and second sections are adapted to receive a compression force moving the two sections relatively toward each other, whereby at least some of the fingers move outwardly so as to secure the two sections in the bore in the medium.

20 Claims, 5 Drawing Sheets

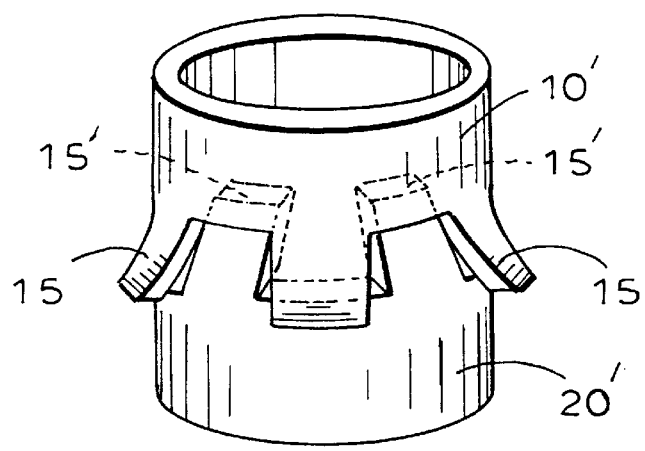
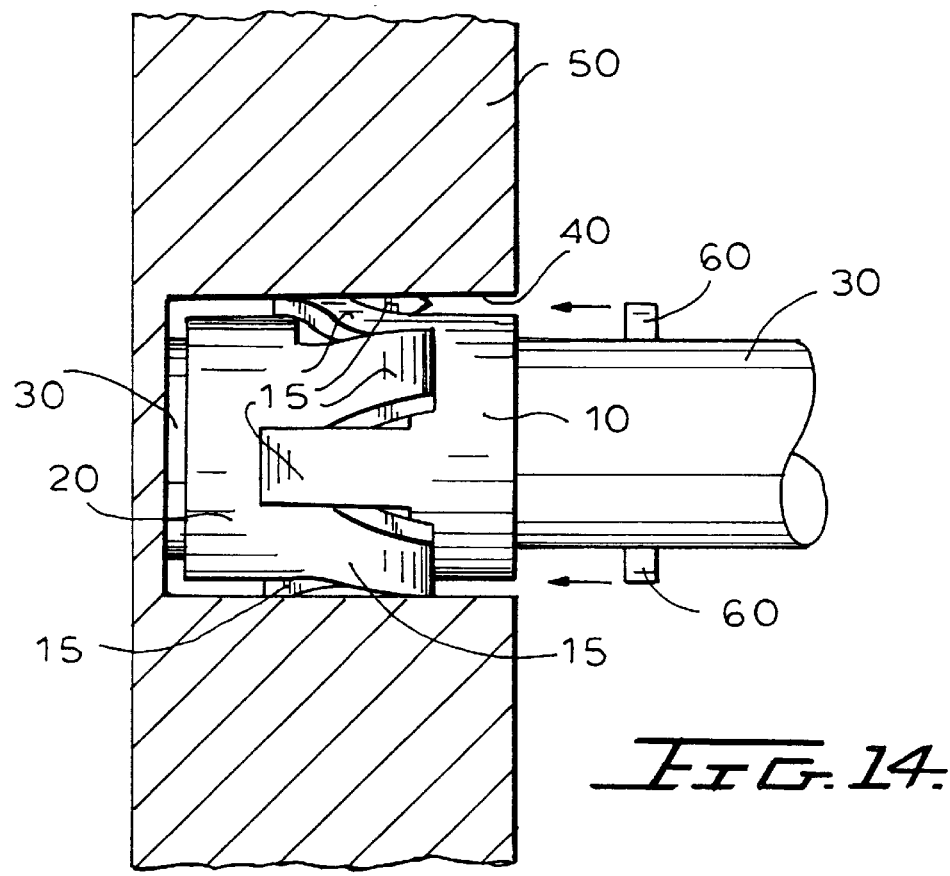

ANCHOR AND METHOD FOR SECUREMENT INTO A BORE

This is a continuation of application Ser. No. 08/294,067, filed Aug. 22, 1994. Now U.S. Pat. No. 5,645,589.

BACKGROUND OF THE INVENTION

The present invention relates to anchoring devices and methods and, in particular, to anchors for securement in bores in first members and which allow attachment of second members to the first members. The invention accordingly relates to devices for coupling a second member, i.e., a cylindrical or tubular member, into a bore in a first member. The present invention is particularly applicable in the medical field, but also has application in other fields, for example, the general field of fasteners and in the construction industry.

There is a need for a simple acting and quickly installable device for coupling a second member into a bore in a first member. There is particularly a need for such a device in the medical and surgical fields. In particular, there is a need for such a device which can be used to connect tissues or bones to other tissues or bones. Furthermore, there is a need for a device which will allow manmade materials to be connected to tissue or bones, in particular, to allow cylindrical or rod shaped objects, e.g., prosthesis, to be fastened to a bore in a bone or other tissue. There is furthermore a need for an easily installable device for anchoring or fastening sutures to tissue, which sutures can then be connected to another object, for example, other tissue.

In the medical and surgical fields, there is a particular need for a device which can be coupled to a first object which is then inserted into a bore in the second object, thereby to quickly lock the first and second objects together. For example, there is a need for such a device which can connect prostheses to bone or bone to bone. There is furthermore a need for such a connection device which is essentially hollow in the interior thereby to allow placement of parts of tissue, bone or manmade materials inside the device, such as rods, pins, valves, sutures, etc.

There is also a need for a device which can lock two objects together in a quick and simple manner, for example, by compression, thereby to lock a component inside the device and simultaneously to a medium, for example, bone. There is a need for such a device for locking two components together, for example, bone and bone or tissue and bone or tissue and tissue, and which device can be left hollow to allow fluid to pass through the inserted device. There is furthermore a need for such a device which can direct or inhibit the flow of fluid passing through the device. Such a device could be used in the medical field to connect bone to bone, for example, to repair fractures or in spinal surgery. Such a device could also be used to connect other materials to bone, for example, prostheses to bone. These could be used in hip prostheses, knee prostheses or as bone plugs and dental implants.

There is furthermore a need for such a connection device which allows connection of tissue to bone. This could be used for ligament repair, meniscus repair and soft tissue repair. There is also a need for such a device which can provide tissue to tissue connections, for example, liver, lung and spleen resections.

There is also a need for such a device which allows materials to be connected to tissue. Such a device could be used in applications involving stenoses to provide clear passageways in esophageal, prostate and coronary tracts through the hollow center of the device, as filters and valves to block and emboli and as dams, for example, pancreatic blockers.

There is furthermore a need for a quick connection device which can be used in the fastener and construction industry and which allows connection of first objects into bores located in second objects.

Various anchoring, quick connection devices and devices for securement in blind holes are known. For example, in U.S. Pat. Nos. 2,143,086, 2,100,570, and 5,161,916, a screw is fastened in a bore by the action of an expandable member, for example, a tubular element enlarged by a conical member. In U.S. Pat. No. 1,247,621, a screw is fastened in a bore by the action of an expandable member comprising expandable wings. In U.S. Pat. No. 4,293,259, expandable locking elements which fit into an undercut provide anchoring.

In each of the above patents, a screw element causes the expandable members, generally through the intermediary of a conical element, which may be a part of the screw or separate from the screw, to expand to grab the inner surface of the bore to provide the attachment.

In another patent, U.S. Pat. No. 5,094,563, two interdigitated spacers are provided which allow the securement of an element to a wall having a hollow construction. In this patent, the interdigitated fingers are used to provide support between the skins of the hollow wall to prevent collapse of the wall.

U.S. Pat. No. Re.34,293 shows a ligament attachment method which works on a similar principle to the construction fasteners described above, i.e., employing an expandable element which is expanded by a conical element operated by a screw. U.S. Pat. No. 5,037,422 discloses a bone anchoring device for securing sutures to bone. The device is conically shaped with serrations on the external surface. The device is forced into a recess in the bone and the conical shape and serrations keep it secured in the bone.

None of the prior art devices, however, provides a simple, quick and secure fastening device, which is especially adaptable in the medical field, for securing two objects, such as bone, tissue or foreign objects, together.

SUMMARY OF THE INVENTION

It is an object of the present invention to provide an anchoring device for securement in a bore in a medium.

It is also an object of the present invention to provide a connection device for connecting a first object to a bore in a second object and, particularly such a connection device which is simple to use and quick acting.

It is yet still a further object of the present invention to provide such a connection device which is suitable for the medical and surgical fields.

It is yet still a further object of the present invention to provide such a device which is suitable for use with bone, tissue or foreign objects, for example, prosthetic materials or any combinations thereof.

It is yet still a further object of the present invention to provide a quick connect fastener for the construction industry and the fastener industry in general.

It is yet still a further object of the present invention to provide such a quick connection device which also allows the implantation of sutures in tissue or bone or other biological matter where sutures cannot be applied directly to the matter.

The above and other objects of the present invention are achieved by an anchor for securement into a bore in a medium comprising a first generally hollow cylindrical section having a first plurality of spaced longitudinally directed fingers; a second generally hollow cylindrical section having a second plurality of spaced longitudinally directed fingers; the first and second sections being arranged opposed to each other with the fingers of each section being interdigitated with the fingers of the other section; the first and second sections being adapted to receive a compression force moving the two sections relatively toward each other, whereby at least some of the fingers move outwardly so as to secure the two sections in the bore in the medium.

The objects of the invention are also achieved by a method for securing an anchor in a bore in a medium comprising providing a first generally hollow cylindrical section having a first plurality of spaced longitudinally directed fingers; providing a second generally hollow cylindrical section having a second plurality of spaced longitudinally directed fingers; arranging the first and second sections opposed to each other with the fingers of each section interdigitated with the fingers of the other section; and applying a compression force to the first and second sections to move the two sections relatively toward each other, whereby at least some of the fingers move outwardly so as to secure the two sections in the bore in the medium.

Other features and advantages of the present invention will become apparent from the following description of the invention which refers to the accompanying drawings.

BRIEF DESCRIPTION OF THE DRAWINGS

The invention will now be described in greater detail in the following detailed description with reference to the drawings in which:

FIG. 8 is a perspective view of the device of FIG. 6 showing how it would appear after activation in a bore (not shown);

FIG. 14 shows the device of FIG. 1 actually in place in a bore in matter, showing how it has been used to secure a cylindrical object in the bore.

DETAILED DESCRIPTION OF THE INVENTION

Figure 1:
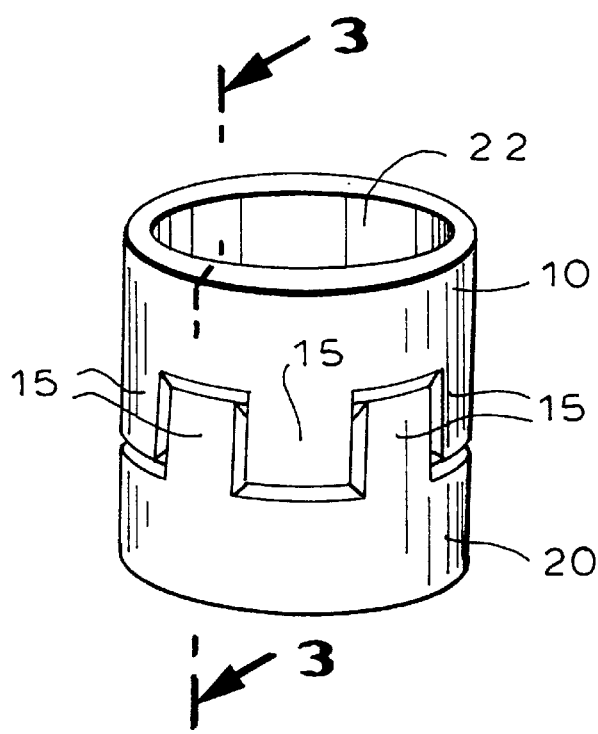
FIG. 1 is a perspective view showing a first embodiment of a quick connection device of the present invention before the device is activated to allow its securement in a bore.

With reference now to the drawings, FIG. 1 shows a first embodiment of the fixation device according to the present invention. FIG. 1 shows the device prior to use. The device includes two sections 10 and 20. In the device shown in FIG. 1, the two sections 10 and 20 are identical, but they need not be identical. In other embodiments shown in the drawings, the two sections are not necessarily identical.

The two sections 10 and 20 each have a group of fingers 15 which interdigitate with the fingers of the other section. The sections 10 and 20 can be made of any suitable material, hard or soft, depending on the application. The material must have a requisite degree of flexibility or deformability, since the fingers 15 must be allowed to bend to accomplish the fixation function, as will be described in more detail below. Suitable materials might be biocompatible metals if used in the medical field, plastics or any metal or plastic having the requisite flexibility or deformability if used as a general construction fastener.

Figure 2:
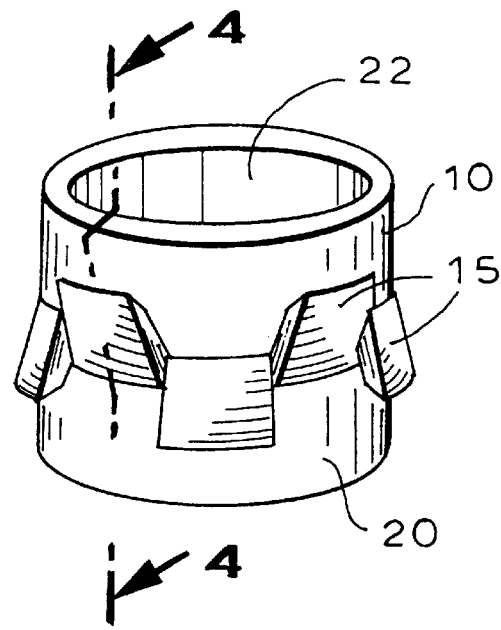
FIG. 2 shows the invention of FIG. 1, but showing how the device appears after activation to allow its securement in a bore in a medium, not shown.

In order to use the device, a first object, for example, a cylinder or rod 30, as shown in FIG. 14, is placed inside the opening 22 of the section 10 and fixed to the opening 22 of the second section 20. The object 30 can be fixed to the section 20 by any suitable means, depending on the application and the composition of the elements 20 and 30. For example, suitable affixation techniques might comprise, e.g., gluing, or welding. Preferably, the section 10 is sized such that the object 30 to be secured is a close fit within the opening 22. The interdigitated sections 10 and 20 surrounding the object 30 are then placed into the bore 40 in the object 50 into which the object 30 is to be secured. Preferably, the outer diameter of the sections 10 and 20 is sized such that it is a close fit within the bore 40. A device not shown in detail, but shown schematically, for example, at 60 in FIG. 14, and which may surround the object 30 secured in the interior of the sections 10 and 20, is then used to compress the two sections 10 and 20 together. For example, section 10 can be forced into section 20. If the object 50 into which the anchor of the invention is to be secured is not of sufficient strength so as to take up an axial force, it is desirable at the same time that device 60 presses section 10 into section 20, simultaneously to support object 30 against movement. This prevents section 20, which has been secured to object 30 (e.g. by welding or gluing) from moving and thereby exerting an axial force on object 50. FIG. 2 shows the device after the two sections 10 and 20 have been moved relatively toward each other.

The compression force has the effect of forcing outwardly the interdigitated fingers 15 on each of the sections 10 and 20. The effect of forcing the fingers 15 outwardly is to lock the two sections 10 and 20 into the bore 40. The tips of the fingers extending in opposite directions frictionally secure the device in the bore against longitudinal movement outwardly and inwardly. At the same time that the sections 10 and 20 are locked into the bore 40, the compression effect forces the opening 22 to a decreased diameter, causing the object 30 also to be fastened securely to the section 10, and therefore inside the bore 40 in the object 50.

Figure 3:
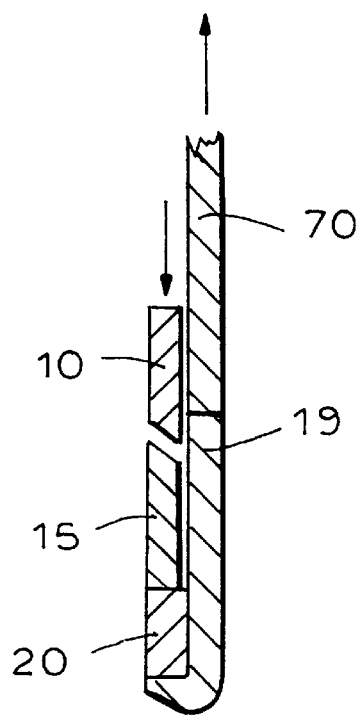
FIG. 3 is a cross-section along lines 3—3 of FIG. 1 and also adding a sleeve member.
Figure 4:
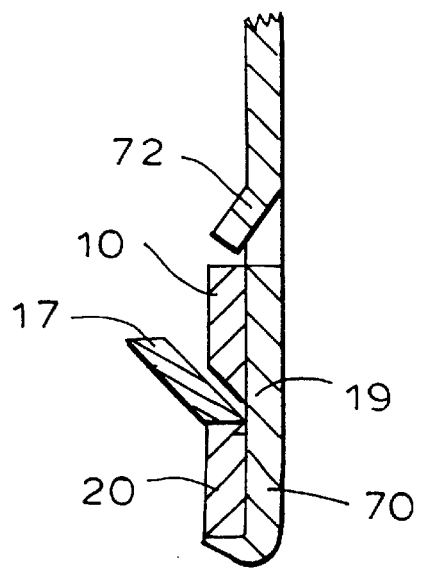
FIG. 4 is a cross-section along lines 4—4 of FIG. 2 also adding a sleeve member.
Figure 5:
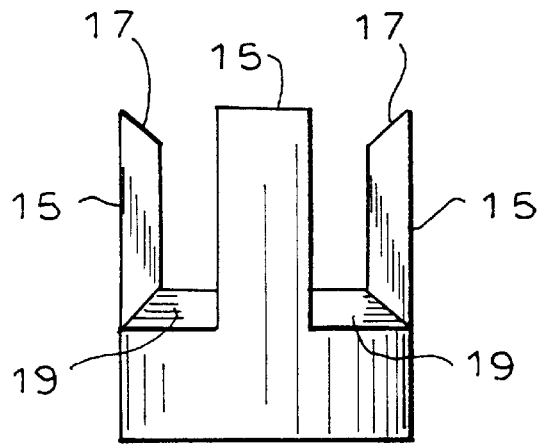
FIG. 5 is a plan view of one portion of the device of FIG. 1.
Figure 5A:
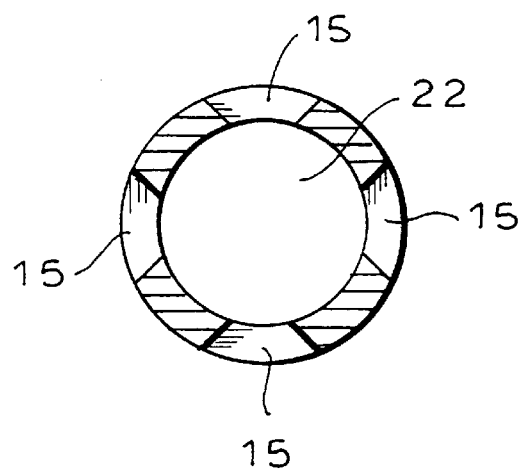
FIG. 5A is a top view of the device shown in FIG. 5.

In order to facilitate the outward movement of the fingers 15, they are preferably made such that they have tapered portions 17 as shown most clearly in FIGS. 3, 4 and 5. Additionally, between the fingers, the sections 19 are also tapered, as shown in FIG. 5, to facilitate outward movement of the fingers 15 when the sections 10 and 20 are forced together.

Figure 6:
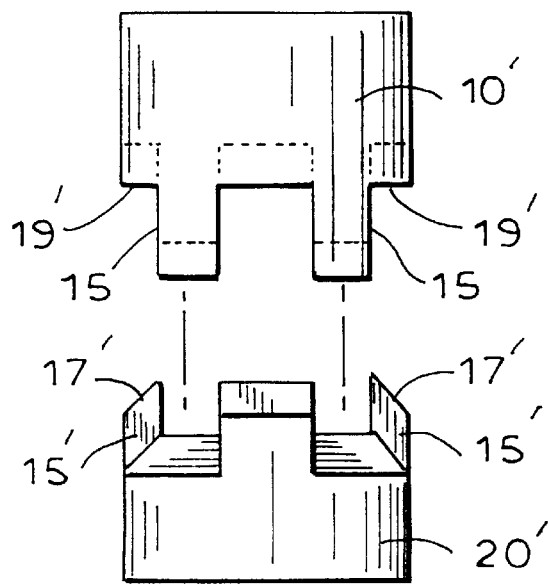
FIG. 6 is a plan view of a second embodiment of the device according to the present invention.
Figure 7:
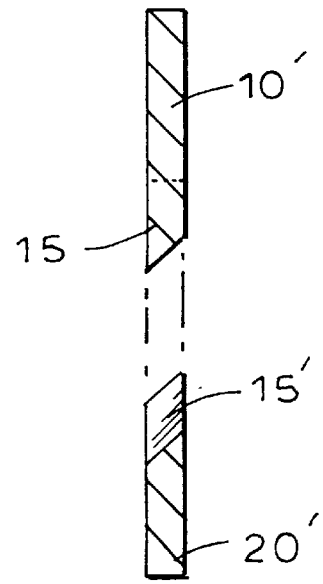
FIG. 7 is a cross-section along the lines VII—VII of FIG. 6.

FIG. 6 shows a second embodiment of the present invention. In this embodiment, the two sections 10' and 20' are different. Section 10' is similar to section 10 of FIG. 1 with the exception that the tapers 19' are reversed, i.e., they taper inwardly, not outwardly. Section 20', is further different, having fingers 15' which have ends 17' tapering opposite those shown, for example, in FIG. 5. In addition, section 10' is also different than section 10 of FIG. 1 in that the sections 19' taper opposite to those shown, for example, in FIGS. 1 or 5. The reason for this is to allow the fingers 15' which interdigitate between the fingers 15 of section 10' to flex inwardly, instead of outwardly. This allows even greater securement of the object, for example, object 30, in the opening 22 through the center of the sections 10' and 20'.

Although the embodiment of FIG. 1 and the embodiment of FIG. 6 are different in several respects, they accomplish essentially the same purpose of securing or anchoring an object 30 into a bore 40 in another object 50. The device 1 provides a lesser degree of frictional engagement with the object 30 because the fingers 15 all flex outwardly, but it provides a greater degree of torsional rigidity because the fingers are arranged such that their sides are adjacent. In the device shown in FIG. 6, although the fingers are interdigitated, the sides of the fingers do not abut for as great a length once the two sections 10' and 20' have been forced together. This is shown in FIG. 8.

FIG. 8 shows the second embodiment according to FIG. 6 after the two sections 10' and 20' have been moved toward each other to force the fingers 15 outwardly and the fingers 15' inwardly.

As shown in FIGS. 3 and 4, a sleeve 70 can also be provided in the interior 22 between the sections 10 and 20 and the object 30 located in the opening 22. The sleeve 70 may have a tang 72 provided thereon which can be used to achieve the relative movement of the two sections 10 and 20 towards each other and therefore the fixation of the device.

Figure 9:
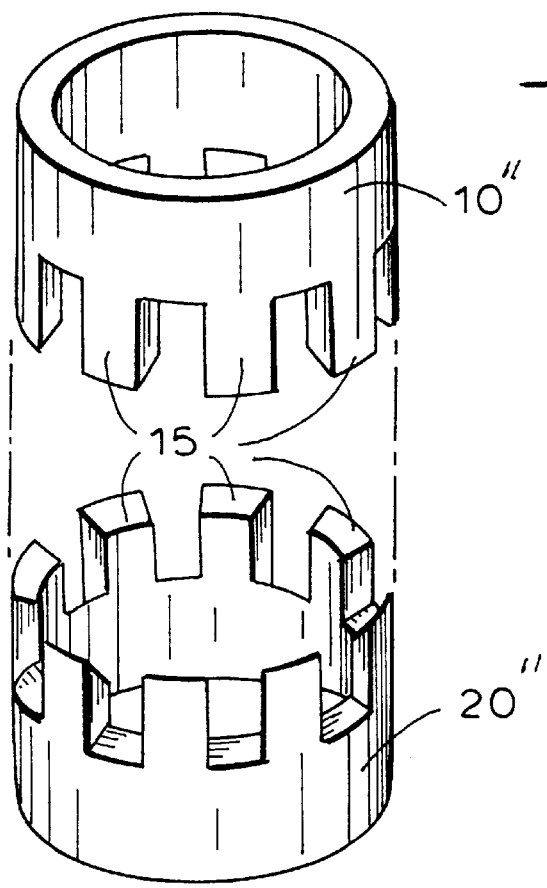
FIG. 9 is a perspective view of another embodiment according to the present invention.

FIG. 9 shows an additional embodiment of the invention having a greater number of interdigitated fingers 15 on each section 10" and 20". In all other respects, this device is similar to that shown in FIG. 1, but provides a greater degree of frictional securement and resistance to torsional movement.

Figure 10:
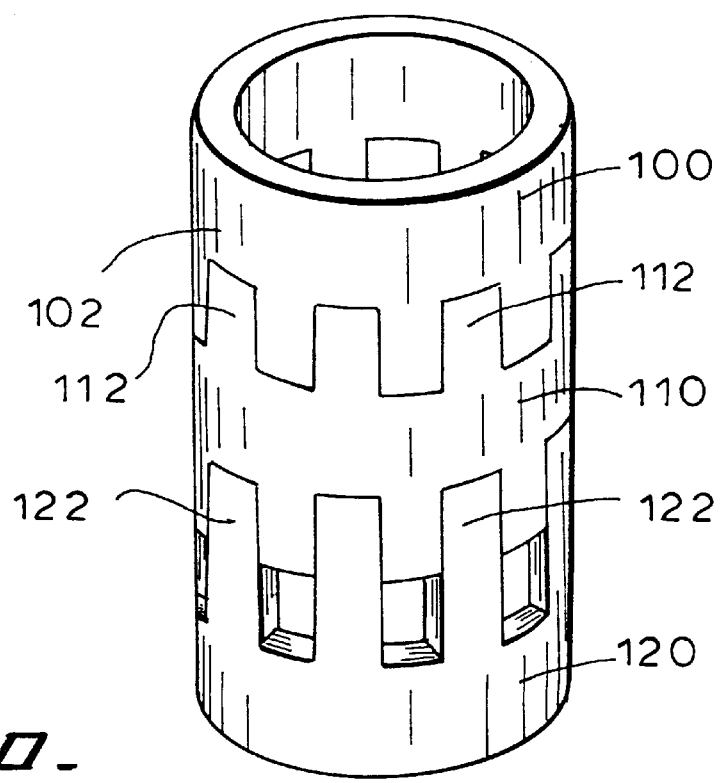
FIG. 10 is a perspective view of yet another embodiment according to the present invention.

FIG. 10 shows yet another embodiment according to the present invention which comprises three sections 100, 110 and 120. When the three sections 100, 110 and 120 are collectively compressed together, the fingers 102, 112, 114 and 122 all move outwardly or inwardly, or in any combination, to achieve any desired degree of fasting. For example, fingers 122 and 102 can move outwardly while fingers 112 and 114 can move inwardly. The particular movement of the fingers is effected by the way the ends of the fingers and the areas between the fingers are tapered, as discussed with respect to the embodiment of FIG. 1.

Figure 11:
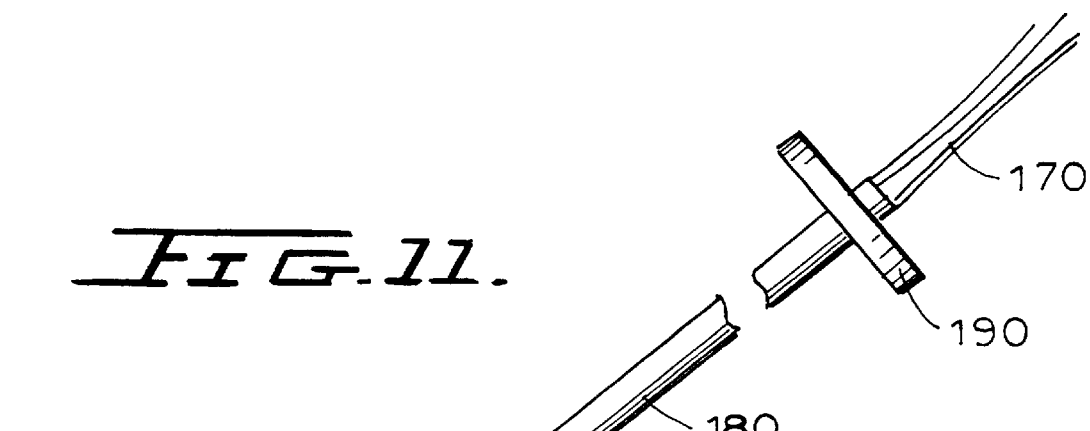
FIG. 11 is a perspective view of yet still another embodiment according to the present invention which comprises a device for anchoring sutures in biological matter.
Figure 12:
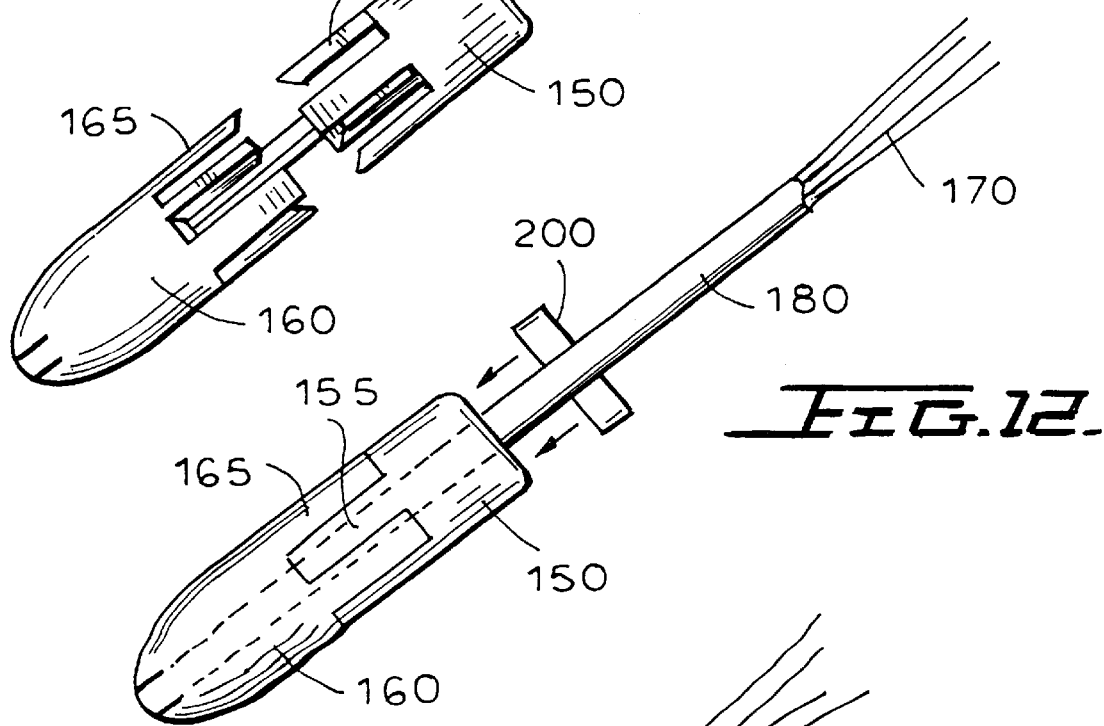
FIG. 12 shows the device of FIG. 11 prior to insertion into biological matter not shown.
Figure 13:
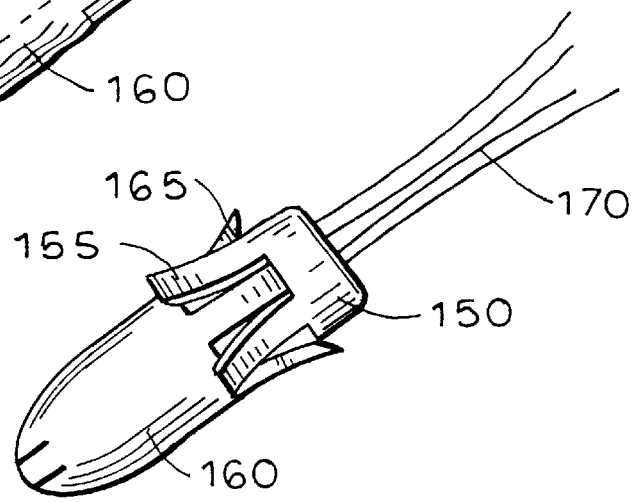
FIG. 13 shows the device of FIGS. 11 and 12 after it has been inserted into a bore in biological matter not show.

FIGS. 11–13 show a further embodiment according to the present invention which allows sutures to be anchored to an object, for example, biological tissue, to which they could not otherwise be ordinarily easily fastened. The device according to FIGS. 11–13 comprises a section 150 and a section 160. Sections 150 and 160 each have interdigitated fingers 155 and 165, respectively. Sutures 170 are fastened to a lower end of the section 160, as shown at 172. The sutures are fed through the center of the section 160, and through the center of the section 150. An insertion tube 180 may be provided which is disposed through the center of section 150. The sutures are fed through the hollow center of the tube 180. Prior to use, the two sections 150 and 160 are arranged as shown in FIG. 12, with their fingers 155 and 165 closely abutting, but without any of the fingers being flexed out of the volumes defined by the cylindrical sections 150 and 160. The tube 180 forms a snug fit in at least the interior of the section 150 although it may also be a snug fit in the interior of the section 160. However, this is not necessary because the interdigitated fingers 155 will keep the section 160 secured to the section 150, at least for the purpose of insertion of the sections 150 and 160 into an opening.

The sections 150 and 160 are thereafter inserted into the opening in the member to which sutures are to be attached in the condition in which they are shown in FIG. 12. After insertion into the opening, a suitable pulling force can be exerted on the sutures by drawing up on them against a handle 190. This will cause the section 160 to move toward the section 150, causing the fingers 155 and 165 to move outwardly, as shown in FIG. 13, thereby securing the sections 10 and 20 in the opening in the biological matter. Alternatively, another device 200 which fits around the outer diameter of the tube 180 can be forced against the section 150, pushing it downwardly while pulling up on the sutures 170, thereby causing the two sections 150 and 160 to move relatively toward each other.

After the two sections 150 and 160 are moved relatively towards each other, the tube 180 is removed from the section 150, for example, by maintaining pressure on the device 200 so that the section 150 is maintained in position. The sutures 170 have now been anchored or secured in the opening in the biological matter by the action of the fingers 155 and 165 of the sections 150 and 160 securing themselves into the opening. The sutures 170 can now be used to secure another object, for example, other tissue, to the biological matter.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A medical anchor for securement into a substantially cylindrical bore formed in a living body, the bore defined by a bore sidewall and an opening into the bore, the anchor comprising:

a first generally hollow biocompatible section having a plurality of spaced longitudinally directed fingers pointed proximally toward the opening when positioned in the bore, the fingers having free ends;

a second biocompatible section proximally disposed with respect to the first section and having a plurality of cam surfaces for engagement with proximally extending surfaces of the plurality of spaced longitudinally directed fingers of the first section;

the first and second sections being arranged opposed to each other with the fingers of the first section being arranged opposed respective cam surfaces of the second section;

an elongated body mechanically engaged with the first section;

the first and second sections being adapted to receive a compression force provided at least in part by the elongated body without rotational movement of the elongated body, the compression force moving the two sections relatively toward each other, the first and second sections having a combined longitudinal size such that they are entirely received within the bore after the compression force is applied, the first section being relatively longitudinally movable with respect to the second section with the fingers of said first section being urged to move outwardly by respective ones of the cam surfaces during the relative longitudinal movement, the free ends of the fingers of the first section being adapted to penetrate into the bore sidewall to secure the first section in the bore without anchoring the elongated body at the opening into the bore;

the elongated body extending in the longitudinal direction of the fingers with the free ends of the fingers pointing toward the elongated body;

at least one of the first and second sections being slidable along the elongated body without relative rotational movement of the elongated body and the at least one section.

2. The anchor recited in claim 1, wherein the elongated body is releasably connected to the first section.

3. The anchor recited in claim 1, wherein each of the fingers have tips, the tips being tapered to facilitate movement of the fingers outwardly.

4. The anchor recited in claim 1, wherein the two sections comprise a biocompatible metal.

5. The anchor recited in claim 1, wherein the sections comprise a biocompatible plastic.

6. The anchor recited in claim 1, further comprising a suture connected to at least one of the two sections.

7. A medical anchor for securement into a bore formed in a living body, the bore defined by a bore side wall and an opening into the bore, the anchor comprising:

a first generally hollow biocompatible section having a first plurality of spaced longitudinally directed fingers pointed toward the opening;

a second generally hollow biocompatible section having a second plurality of spaced longitudinally directed fingers;

the first and second sections being arranged opposed to each other with the fingers of each section being interdigitated with the fingers of the other section;

the first and second sections being adapted to receive a compression force moving the two sections relatively toward each other, said two sections being relatively longitudinally movable with one plurality of fingers moving outwardly and the other plurality of fingers moving inwardly during the relative longitudinal movement, the outwardly moving fingers being adapted to penetrate into the bore side wall to secure the two sections in the bore, the inwardly moving fingers being adapted to grip an elongated body disposed concentrically in at least one of the sections.

8. The anchor recited in claim 7, wherein the fingers of each plurality of fingers have tips, the tips being tapered to facilitate movement of the fingers respectively outwardly or inwardly.

9. The anchor recited in claim 7, wherein each section has a rim portion between fingers, the rim portion being tapered to facilitate movement of the fingers respectively outwardly or inwardly.

10. The anchor recited in claim 9, wherein the tips of the fingers are tapered toward or away from the hollow center of a respective section.

11. The anchor recited in claim 7, wherein the two sections comprise a biocompatible metal.

12. The anchor recited in claim 7, wherein the sections comprise a biocompatible plastic.

13. The anchor recited in claim 7, further comprising a suture connected to at least one of the two sections.

14. A method for securing a medical anchor in a bore formed in a living body, the bore defined by a bore side wall and an opening into the bore, the method comprising:

providing a first generally hollow biocompatible section having a first plurality of spaced longitudinally directed fingers pointed toward the opening;

providing a second generally hollow biocompatible section having a second plurality of spaced longitudinally directed fingers;

arranging the first and second sections opposed to each other with the fingers of each section interdigitated with the fingers of the other section;

applying a compression force to the first and second sections to move the two sections relatively toward each other, said two sections being relatively longitudinally movable with one plurality of fingers moving outwardly and the other plurality of fingers moving inwardly during the relative longitudinal movement, the outwardly moving fingers being adapted to penetrate into the bore side wall to secure the two sections in the bore, the inwardly moving fingers being adapted to grip an elongated body disposed concentrically in at least one of the sections.

15. The method for securing an anchor recited in claim 14, wherein the fingers of each plurality of fingers have tips, and further comprising tapering the tips to facilitate movement of the fingers respectively outwardly or inwardly.

16. The method for securing an anchor recited in claim 14, wherein each section has a rim portion between fingers, and further comprising tapering the rim portion to facilitate movement of the fingers respectively outwardly or inwardly.

17. The method for securing an anchor recited in claim 16, further comprising tapering the tips of the fingers toward or away from the hollow center of a respective section.

18. The method for securing an anchor recited in claim 14, wherein the steps of providing the two sections comprise providing sections made of biocompatible metal.

19. The method for securing an anchor recited in claim 14, wherein the steps of providing the sections comprises providing sections made of biocompatible plastic.

20. The method for securing an anchor recited in claim 14, further comprising connecting a suture to at least one of the two sections.

* * * * *